United States Patent
Miller

(10) Patent No.: US 7,507,830 B2
(45) Date of Patent: *Mar. 24, 2009

(54) PROCESS FOR PREPARING UNSYMMETRICAL BIARYLS AND ALKYLATED AROMATIC COMPOUNDS FROM ARYLNITRILES

(75) Inventor: Joseph A. Miller, Greenville, NC (US)

(73) Assignee: Pharmacore, Inc., High Point, NC (US)

( * ) Notice: Subject to any disclaimer, the term of this patent is extended or adjusted under 35 U.S.C. 154(b) by 674 days.

This patent is subject to a terminal disclaimer.

(21) Appl. No.: 10/949,711

(22) Filed: Sep. 23, 2004

(65) Prior Publication Data

US 2005/0124808 A1    Jun. 9, 2005

Related U.S. Application Data

(63) Continuation of application No. 10/202,483, filed on Jul. 23, 2002, now Pat. No. 6,962,999.

(60) Provisional application No. 60/308,003, filed on Jul. 25, 2001.

(51) Int. Cl.
  *C07D 211/78* (2006.01)
  *C07D 211/72* (2006.01)
  *C07D 263/12* (2006.01)
  *C07D 307/02* (2006.01)
  *C07C 41/00* (2006.01)

(52) U.S. Cl. ............... 546/286; 546/304; 568/626; 548/239; 549/506

(58) Field of Classification Search ............ 546/286, 546/304; 568/626; 548/239; 549/506
See application file for complete search history.

(56) References Cited

U.S. PATENT DOCUMENTS

| | | | |
|---|---|---|---|
| 4,730,032 A | 3/1988 | Rossi et al. | |
| 4,912,276 A | 3/1990 | Puckette | |
| 5,128,355 A | 7/1992 | Carini et al. | |
| 5,130,439 A | 7/1992 | Lo et al. | |
| 5,288,895 A | 2/1994 | Bouisset et al. | |
| 5,364,943 A | 11/1994 | Rosen et al. | |
| 5,559,277 A | 9/1996 | Beller et al. | |
| 5,874,606 A | 2/1999 | Huang et al. | |
| 5,922,898 A | 7/1999 | Miller et al. | |
| 6,194,599 B1 | 2/2001 | Miller et al. | |
| 6,962,999 B2 * | 11/2005 | Miller | 546/286 |

FOREIGN PATENT DOCUMENTS

| | | |
|---|---|---|
| EP | 0 131 968 A2 | 1/1958 |
| EP | 0 470 795 B2 | 2/2001 |

OTHER PUBLICATIONS

Cibulka, Collect Czech Chem Commun, vol. 64, pp. 1159-1179, 1999.
Ali et al., 1992, "Palladium-catalysed cross-coupling reactions of arylboronic acids with π-deficient heteroaryl chlorides," *Tetrahedron* 48(37):8117-8126.
Bleicher and Cosford, 1995, "Aryl- and heteroaryl-alkyne coupling reactions catalyzed by palladium on carbon and CuI in an aqueous medium," *SYNLETT* 11:1115-1116.
Bringmann et al., 1990, "The directed synthesis of biaryl compounds: modern concepts and strategies," *Angew. Chem. Int. Ed. Engl.* 29:977-991.
Carini et al., 19991, "Nonpeptide angiotensin II receptor antagonists: the discovery of a series of N-(biphenylylmethyl)imidazoles as potent, orally active antihypertensives," *J. Med. Chem.* 34:2525-2547.
Clough et al., 1976, "Coupling of nonequivalent aromatic rings by soluble nickel catalysts. A general route to the 1,8-diarylnaphthalenes," *J. Org. Chem.* 41(13):2252-2255.
Kalinin, V. N., 1992, "Carbon-carbon bond formation in heterocycles using NI- and Pd-catalyzed reactions," *Synthesis* pp. 413-432.
Mantlo et al., 1991, "Potent, orally active imidazol[4,5-b]pyridine-based angiotensin II receptor antagonists," *J. Med. Chem.* 34:2919-2922.
Miller and Farrell, 1998, "Preparation of unsymmetrical biaryls via Ni- or Pd-catalyzed coupling of aryl chlorides with arylzincs," *Tetrahedron Letters* 39:6441-6444.
Miller and Farrell, 1998, "Synthesis of functionally substituted unsymmetrical biaryls via a novel double metal catalyzed coupling reaction," *Tetrahedron Letters* 39:7275-7278.
Miyaura et al., 1981, "The palladium-catalyzed cross-coupling reaction of phenylboronic acid with haloarenes in the presence of bases," *Synthetic Communications* 11(7):513-519.
Negishi et al., 1977, "Selective Carbon-carbon bond formation via transition metal catalysis. 3. A highly selective synthesis of unsymmetrical biaryls and diarylmethanes by the nickel- or palladium-catalyzed reaction of aryl- and benzylzinc derivatives with aryl halides," *J. Org. Chem.* 42(10):1821-1823.

(Continued)

*Primary Examiner*—James O Wilson
*Assistant Examiner*—Ebenezer Sackey
(74) *Attorney, Agent, or Firm*—Samuel B. Rollins; Lyman H. Smith

(57) ABSTRACT

Methods are provided for the construction of unsymmetrical biaryl compounds and alkylated aromatic compounds from arylnitriles using a nickel or palladium catalyzed coupling in which the catalyst has at least one phosphine or phosphite ligand.

10 Claims, 1 Drawing Sheet

OTHER PUBLICATIONS

Pridgen, L. N., 1982, "Oxazolines. 3. Regioselective synthesis of 2-(monosubstituted phenyl) and/or unsymmetrically 2-(disubstituted phenyl) 2-oxazolines by cross-coupling Grignard reagents to (haloaryl)-2-oxazolines," *J. Org. Chem.* 47:4319-4323.

Sainsbury, M., 1980, "Modern methods of aryl-aryl bond formation," *Tetrahedron* 36:3327-3359.

Stanforth, S. P., 1998, "Catalytic cross-coupling reactions in biaryl synthesis," *Tetrahedron* 54:263-303.

Saito et al., 1996, "A synthesis of biaryls via nickel(0)-catalyzed cross-coupling reaction of chloroarenes with phenylboronic acids," *Tetrahedron Letters* 37(17):2993-2996.

Tamao et al., 1976, "Nickel-phosphine complex-catalyzed Grignard coupling. I. Cross-coupling of alkyl, aryl, and alkenyl Grignard reagents with aryl and alkenyl halides: general scope and limitations," *Bulletin of the Chemical Society of Japan* 49(7):1958-1969.

Whittall et al., 1996, "Organometallic complexes for nonlinear optics. 3. Molecular quadratic hyperpolarizabilities of ene-, imine, and azo-linked ruthenium α-acetylides: X-ray crystal structure of Ru((E)-4,4'-C≡CC6H4CH:CHC6H4NO2)(Pph3)(n-C5H5)," *Organometallics* 15(7):1935-1941 (Abstract).

Zhu et al., 1991, "The direct formation of functionalized alkyl(aryl)zinc halides by oxidative addition of highly reactive zinc with organic halides and their reactions with acid chlorides, α,β-unsaturated ketones, and allylic, aryl and vinyl halides," *J. Org. Chem.* 56:1445-1453.

Silbille et al., 1992, "Electrochemical conversion of functionalized aryl chlorides and bromides to arylzinc species," *J. Chem. Soc., Chem. Commun.* pp. 283-284.

Fuson, R.C. and W.S. Friedlander: "Displacement of substituents in phenyl 2,4,6-triisoplyphenyl ketone by the action of Grignard reagents;" J. Am. Chem. Soc.; vol. 75, pp. 5410-5411 (1953).

Fuson, R.C. et al.: "The reaction of Grignard reagents with the cyanobenzoyldurenes;" *J. Org. Chem.*; vol. 16, pp. 648-654 (1951).

Miller, J. A.: "C-C Bond activation with selective functionalization: preparation of unsymmetrical biaryls from benzonitriles;" Tetrahedron Letters; vol. 42, pp. 6991-6993 (2001).

Milner, D.J.: "The mono-alkyldecyanation of tetrafluoroterephtalonitrile by reaction with Grignard reagents;" J. Organometallic Chem.; vol. 302, pp. 147-152 (1986).

* cited by examiner

PROCESS FOR PREPARING UNSYMMETRICAL BIARYLS AND ALKYLATED AROMATIC COMPOUNDS FROM ARYLNITRILES

CROSS-REFERENCES TO RELATED APPLICATIONS

This application claims priority of application Ser. No. 10/202,483, filed Jul. 23, 2002, which claims the benefit of U.S. Ser. No. 60/308,003 filed Jul. 25, 2001, the disclosures of which are incorporated herein by reference.

STATEMENT AS TO RIGHTS TO INVENTIONS MADE UNDER FEDERALLY SPONSORED RESEARCH AND DEVELOPMENT

Not applicable

REFERENCE TO A "SEQUENCE LISTING," A TABLE, OR A COMPUTER PROGRAM LISTING APPENDIX SUBMITTED ON A COMPACT DISK.

Not applicable

BACKGROUND OF THE INVENTION

A variety of catalytic methods have been described for the preparation of biaryl compounds or for the coupling of alkyl or alkenyl radicals to an aryl group. Reviews of these methods can be found in, for example, Stanforth, *Tetrahedron*, vol. 54 (1998) pp. 263-303; Sainsbury, *Tetrahedron*, vol. 36 (1980), pp. 3327-3359 and Bringman et al., *Angew. Chem. Int. Ed. Engl.*, vol. 29, (1990), 977-991.

In the field of biaryl couplings, the renaissance began in the mid- to late-1970's with the Kharasch reaction in which an aryl Grignard reagent (Ar'MgX, wherein X is halogen) is reacted with an aryl halide (ArX) to produce a biaryl (Ar—Ar') compound. However, a number of functional groups (e.g., aldehydes, ketones, esters and nitro groups) are not compatible with conditions for the Kharasch reaction.

Tamao et al., Bull. Chem. Soc. Japan, vol. 49 (1976), pp. 1958-1969, discloses that arylbromides can be reacted with arylmagnesium halides (aryl Grignard reagents) in the presence of dihalodiphophinenickel complexes to give biaryl compounds. A sole disclosed attempt to react an aryl chloride (chlorobenzene) with an arylmagnesium halide (mesityl) was reported to give only a 6% yield of the desired biaryl. Similar reactions of the bromobenzene with mesitylmagnesium bromide gave yields of 78-96%. This reference states, "The most serious limitation is that the substituents on the organic halides and on the Grignard reagents are restricted to those which cannot react with Grignard reagents."

Clough et al., *J. Org. Chem.*, vol. 41 (1976), pp. 2252-2255 disclose that 1,8-dihalonapthalenes can be reacted with arylmagnesium halides in the presence of certain soluble nickel catalysts to give 1,8-diarylnaphthalenes. The reactivities of the 1,8-dihalonaphthalenes in this system was found to be I>Br>>Cl.

U.S. Pat. No. 4,912,276 discloses that aryl chlorides can be reacted with arylmagnesium halides in the presence of a nickel-triorganophosphine catalyst to give biaryl compounds. The disclosed scope of the aryl groups in the arylchlorides, the arylmagnesium reagents, and the biaryl compounds consists of phenyl and substituted phenyl in which the substituents are those that have previously demonstrated a lack of reactivity with arylmagnesium halides (e.g., alkyl, alkoxy and the like). The only biaryl whose preparation is exemplified by working examples is the symmetrical biaryl 2,2'dimethylbiphenyl, prepared from 2-chlorotoluene and o-tolylmagnesium chloride (derived from 2-chlorotoluene).

Pridgen, *J. Org. Chem.*, vol. 47 (1982), pp. 4319-4323 discloses two examples in which 2-(chlorophenyl)-2-oxazolines are reacted with arylmagnesium halides in the presence of a diphosphine-chelated nickel catalyst to give the corresponding 2-(biaryl)-2-oxazoline compounds. The oxazoline group activates the aryl chloride and provides a form of the carboxyl group that is protected from reaction with the arylmagnesium halide.

U.S. Pat. No. 5,288,895 describes a process for the preparation of 4-methyl-2'-cyanobiphenyl (a.k.a. 2-(4'-methylphenyl)benzonitrile) wherein a 2-halobenzonitrile is reacted with a 4-methylphenyl magnesium halide in the presence of manganous salt. The patent provides examples in which 2-chlorobenzonitrile produces a coupled product (2-(4'-methylphenyl)benzonitrile) with a yield of 60-75% recovered as a "brown viscous liquid". Recrystallizations (plural) are reported to give the product as a beige solid, but the yield of this purified solid is not reported.

Negishi followed Kharasch's work in the mid 1970's with a coupling reaction in which an aryl zinc reagent (Ar'ZnX, wherein X is halogen) is reacted with an aryl halide or triflate (ArX, wherein X is halogen or triflate) to produce a biaryl (Ar—Ar') compound. The zinc reagents used by Negishi are generally more tolerant of functional groups such as esters, aldehydes and ketones. In particular, Negishi et al, *J. Org. Chem.*, vol.42 (1977), pp. 1821-1823 discloses reactions of arylzinc derivatives (arylzinc chloride or diarylzinc) with aryl bromides or iodides in the presence of nickel or palladium complexes as catalysts to produce unsymmetrical biaryls. The arylzinc derivatives were prepared by a metathesis reaction between the corresponding aryllithium and zinc dichloride. Additionally, the authors note the ability of arylzinc derivatives to tolerate various electrophilic functional groups, such as nitrile and ester, in the arylbromide or iodide.

Zhu et al., *J. Org. Chem.*, vol. 56 (1991), pp. 1445-1453 similarly disclose reactions of arylzinc halides with aryl bromides or aryl iodides in the presence of a palladium tetrakis (triphenylphosphine as catalyst to form biaryl compounds. The arylzinc halides were prepared by the reaction of the arylhalide with a form of highly reactive zinc.

Silbille et al., *J. Chem. Soc. Chem. Comm.*, 1992, pp. 283-284 disclose a reaction of 4-trifluoromethylphenylzinc chloride, prepared from 4-trifluoromethyl-chlorobenzene, with 4-bromobenzonitrile using the palladium complex $PdCl_2(PPh_3)_2$ as catalyst to form 4-trifluoromethylphenyl-4'-cyanobiphenyl. This reference also discloses a method of preparing arylzinc halides from arylchlorides and arylbromides, including arylzinc reagents ones bearing various functional groups such as ester, nitrile, or ketone.

Carini et al., *J. Med. Chem.*, vol. 34 (1991), 2525-2547, disclose the preparation of 3-(4'-methylphenyl)benzonitrile by reacting 4-methylphenylzinc halide (prepared from 4-bromotoluene via 4-methylphenylmagnesium bromide, which is reacted with zinc chloride) and 3-bromobenzonitrile in the presence of bis(triphenylphosphine)nickel dichloride as precatalyst. U.S. Pat. No. 5,128,355 (to Carini et al.) similarly shows an equation (Scheme 14, Equation e) representing the nickel catalyzed cross coupling of a methylphenylzinc chloride (isomer unspecified) with a bromobenzonitrile (isomer unspecified) to give a methylphenylbenzonitrile (isomer unspecified). This method is exemplified only for the preparation of 2,6-dicyano-4'-methylbiphenyl from 2,6-dicyanophenylbromide (Example 343).

Mantlo et al., *J. Med. Chem.*, vol. 34 (1991), pp. 2919-2922 discloses the preparation of 2-(4'-methylphenyl)benzonitrile from 4-bromotoluene and 2-bromobenzonitrile according to the method (referenced) of Negishi et al. *J. Org. Chem.*, vol. 42 (1977), pp. 1821-1823. A zinc derivative was formed from the 4-bromotoluene and reacted with the 2-bromobenzonitrile in the presence of a catalytic amount of a dichlorobis (triphenylphosphine)nickel.

By the late 1970's Stille had extended the biaryl coupling repertoire to include the reaction of arylstannanes (Ar'SnR$_3$, wherein R is methyl or butyl) with aryl halides or triflates (ArX, wherein X is halogen or triflate). While this reaction can be run under neutral conditions and is generally compatible with a wide range of aryl substituents, the toxicity of the organotin reagents and byproducts limits the usefulness of this method.

More recently, Suzuki and coworkers developed a coupling reaction in which an aryl boronic acid (Ar'B(OH)$_2$) is reacted with an aryl halide or triflate (ArX, wherein X is halogen or triflate) to produce the biaryl product Ar—Ar'. An early report of this general reaction is Miyaura et al., *Synthetic Communications* vol. 11 (1981), 513. In this reference, chlorobenzene is reported to fail to react with phenylboronic acid using tetrakis(triphenylphosphine)palladium as catalyst in this system.

Ali et al., *Tetrahedron*, vol 48 (1992), pp. 8117-8126 disclose Suzuki-type cross-coupling reactions of arylboronic acids with pi-electron deficient heteroaryl chlorides (chloropyridines, chloropyrimidines, and chloropyrazines, chloroquinolines).

U.S. Pat. No. 5,130,439 discloses a process for preparing certain protected tetrazolyl biphenyls in which a protected tetrazolylphenylboronic acid or boronate derivative is reacted with a substituted phenyl bromide or iodide or a substituted sulfonyloxyphenyl derivative in the presence a base and a nickel, palladium or platinum catalyst, preferably palladium. Three of the working examples (Examples 4, 9, and 12) relate to the disclosed process for preparing the protected tetrazolyl biphenyls, and all involve reactions of triphenylmethyltetrazolylphenylboronic acid with a substituted (4-methyl, 4-hydroxymethyl, 4-formyl) bromobenzene in the presence of a tetrakis(triphenylphosphine)palladium catalyst and a carbonate base. This process has the disadvantage of requiring prior synthesis of the triphenylmethyltetrazolylphenylboronic acid. This reference discloses a process for preparing the triphenylmethyltetrazolylphenylboronic acid from the corresponding bromobenzonitrile by reacting it with tributyltin chloride and sodium azide, then with triphenylmethyl chloride to form the triphyenylmethyltetrazolylphenylbromide, which is reacted sequentially with n-butyllithium and triisopropylborate and the resulting boronate ester is finally hydrolyzed to the boronic acid. This reference illustrates that the nitrile group must be protected, in this case as the triphenylmethyltetrazolyl group, to be compatible with the use of an aryllithium intermediate in the overall process.

European Patent Application 470,795 discloses a process for preparing biphenylcarbonitriles in which a 4-methylphenyl boronic acid or boronate ester is reacted with a bromo-, iodo-, or trifluoromethanesulphonyloxy-benzonitrile in the presence of a palladium or nickel catalyst and a suitable base. Three of the working examples (Examples 1, 2, and 6) relate to the disclosed process for preparing biphenylcarbonitriles, and all involve reactions of the 4-methylphenylboronic acid with 2-bromobenzonitrile in the presence of a palladium catalyst and sodium carbonate.

Saito et al., *Tetrahedron Letters*, vol 37 (1996), pp. 2993-2996 states, "The palladium-catalyzed cross-coupling reaction of arylboronic acids with aryl halides or triflates gives biaryls. High yields have been achieved with many substrates having various functional groups on either coupling partner, when using aryl bromides, iodides, or triflates as an electrophile. Chloroarenes are an economical and easily available, but they have been rarely used for the palladium catalyzed cross coupling reaction of arylboronic acids because of the oxidative addition of chloroarenes is too slow to develop the catalytic cycle. However, chloroarenes have been an efficient substrate for the nickel catalyzed cross coupling reaction with Grignard reagents . . . developed by Kumada and Tamao." This reference (Saito et al.) discloses syntheses of unsymmetrical biaryls by a nickel(0) catalyzed reaction of arylchlorides with arylboronic acids and tripotassium phosphate as the base at elevated temperatures.

U.S. Pat. No. 5,559,277 discloses a process for preparing biaryls by the Suzuki reaction of haloaromatics or arylsulfonates with arylboronates in the presence of a base and certain specific palladium compounds as catalysts. In addition to numerous bromoaromatics, reactions of chloroacetophenone and 2-chlorobenzonitrile are shown in working examples. All the working examples use at least 50% mole excess of the arylboronate relative to the haloaromatic and conduct the reaction for 16 hours at 130° C. The disclosed process also has the disadvantage of requiring the separate preparation of the arylboronate. Example 7 describes the preparation of 2-cyano-4-methylbiphenyl (a.k.a. 2-(4'-methylphenyl)-benzonitrile) from 2-chlorobenzonitrile and 4-methylphenylboronic acid in 73% yield (49% yield on the 4-methylphenylboronic acid).

Kalinin, *Synthesis,* 1992, 413-432 reviews carbon-carbon bond formation to heteroaromatics using nickel and palladium catalyzed reactions and provides numerous examples of the formation of unsymmetrical biaryls, wherein at least one of the aryl groups includes a heteroatom, including examples of palladium catalyzed reactions of arylbromides and aryliodides with arylzinc halides, palladium catalyzed reactions of chloropyridines with arylmagnesium halides, and nickel catalyzed reactions of arylchlorides and arylbromides with arylmagnesium halides.

U.S. Pat. No. 5,364,943 discloses the preparation of 3-amino-2-phenylpyridine and two 3-(substituted benzylamino)-2-phenylpyridine derivatives by the reaction of the corresponding 3-amino-2-chloropyridine or N-benzyl derivative with phenyl magnesium bromide in the presence of bis(phosphine)nickel dichloride complexes. For the parent compound (Example 7), a total of 4.4 eq. of phenylmagnesium bromide was reacted with 3-amino-2-chloropyridine and 0.5 eq. [bis(diphenylphosphino)ethane] nickel(II) chloride over the course of two days, to ultimately obtain a 48% of the isolated product.

Despite the early success with many of these coupling reactions and the continued efforts to refine and extend their applications, further efforts have focused on extending the coupling reactions to multigram or kilogram quantities and to manipulating reaction conditions to increase yields and provide alternatives to the limitations observed with each of the methods described.

For example, in 1998, Miller and Farrell described the preparation of unsymmetrical biaryl via Ni- or Pd-catalyzed coupling of aryl chlorides with arylzincs (see, Miller and Farrell, *Tetrahedron Letters* 39:6441-6444 (1998)). This extension of the Negishi reaction utilized the less expensive and readily available aryl chlorides. See also Miller and Farrell, U.S. Pat. No. 6,194,599 B1, issued Feb. 27, 2001.

Miller and Farrell continued their examination of biaryl couplings, particularly those with reactive functional group substituents. Biaryl compounds having functional groups such as nitriles or esters were efficiently synthesized by the direct Ni- or Pd-catalyzed cross-coupling of aryl halides with arylmagnesium or -lithium reagents (ArM) provided that a catalytic amount of a Zn or Cd salt is also present. See, Miller and Farrell, *Tetrahedron Letters*, 39:7275-7278 (1998) and U.S. Pat. No. 5,922,898, issued Jul. 13, 1999.

Despite these advances, methods for aryl or organometallic couplings on benzonitriles wherein the nitrile group is displaced by the aryl or alkyl portion of an organometallic reagent have not been described. In view of the ready availability of benzonitrile derivatives, such methods would find considerable usefulness in extending the scope of couplings that are currently in use.

Surprisingly, the present invention provides such methods.

BRIEF SUMMARY OF THE INVENTION

In one aspect, the present invention provides a method for the preparation of carbon-carbon bonds, particularly in the preparation of biaryl compounds and alkyl- or alkenyl-substituted aryl compounds. The compounds that are prepared have the general formula Ar'—R, wherein Ar' is a substituted or unsubstituted aryl group, and R is a substituted or unsubstituted alkyl, alkenyl or aryl group. The method described herein uses a nickel or palladium catalyst for the coupling of an arylnitrile (e.g., a benzonitrile or pyridylnitrile) with an organomagnesium reagent (e.g., an alkyl magnesium halide, arylmagnesium halide or alkenylmagnesium halide, as well as related reactive species as described in more detail below) wherein the alkyl, alkenyl or aryl portion of the magnesium reagent is coupled to the site of the arylnitrile that was occupied by the nitrile.

In one group of embodiments, the coupling is a biaryl coupling and can be represented by the reaction:

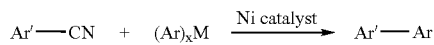

wherein Ar' and Ar are each independently substituted or unsubstituted aryl groups, x is an integer of from 1 to 3, and M represents a magnesium salt (e.g., MgCl, MgBr, MgOtBu, and the like) or an organozinc reagent (e.g., LiZnPh$_3$).

In another aspect, the present invention provides reactions mixtures that are useful in accomplishing the methods described above. Typically, the reaction mixtures contain an arylnitrile (e.g., Ar'—CN), a nickel or palladium catalyst having at least one phosphorus ligand, preferably a phosphine or phosphite ligand, and a suitable organometallic reagent (e.g., a reagent of the formula (R)$_x$-M wherein each R is alkyl, alkenyl or aryl, x is an integer of from 1 to 3 and M is magnesium or zinc, optionally having an additional ligand such as a halide, alkoxide, aryloxide, or thiophenoxide).

In yet another aspect, the present invention provides organomagnesium reagents that are useful in the methods described above. These reagents have the general formula R$^1$MgY$^1$, wherein R$^1$ is substituted or unsubstituted aryl or alkenyl and Y$^1$ is selected from S-aryl, S-(C$_1$-C$_8$)alkyl, P((C$_1$-C$_8$)alkyl)$_2$, P(aryl)$_2$ and P((C$_1$-C$_8$)alkyl)(aryl).

BRIEF DESCRIPTION OF THE DRAWINGS

FIG. 1A illustrates a biaryl coupling reaction in which each of the aryl groups are shown with optional non-interfering substituents (R$^1$, R$^2$, R$^3$ and R$^4$). FIG. 1B illustrates an aryl-alkyl coupling reaction and FIG. 1C illustrates an aryl-alkenyl coupling reaction, with the R groups in each being optional and selected from substituents provided below. In FIGS. 1A-1C, the MgX is shown as an example of the metal species used in coupling. The ligand X can be halogen (e.g., Cl or Br), alkoxide, aryloxide, thioalkoxide, thiophenoxide, dialkylphosphinyl, diarylphosphinyl and the like. FIG. 1D illustrates a biaryl coupling reaction in which the aryl magnesium reagent is converted from a magnesium halide to a magnesium alkoxide to modulate its reactivity.

DETAILED DESCRIPTION OF THE INVENTION

Methods for Coupling to Arylnitriles

Figure 1:
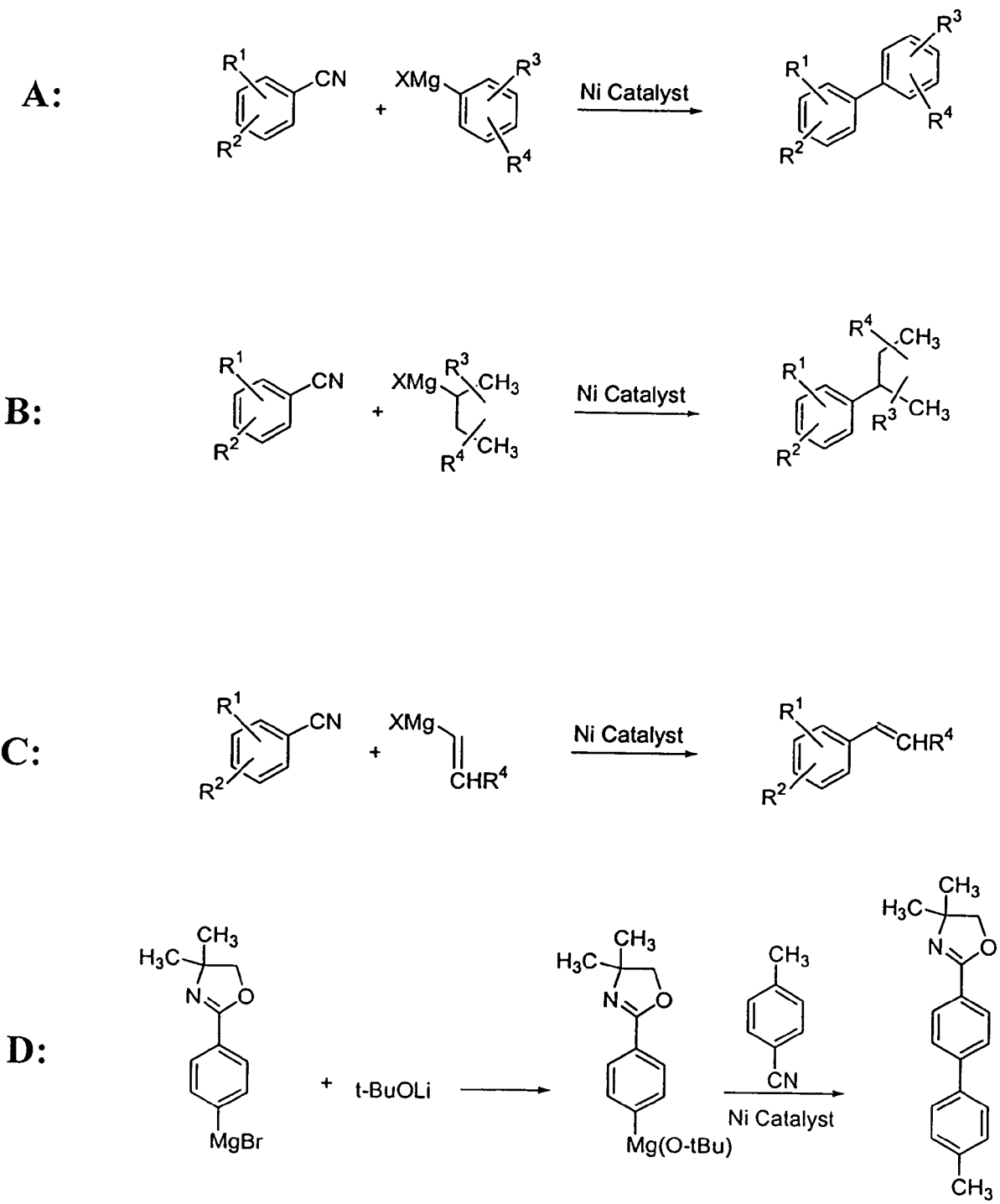
FIG. 1 provides several reactions that illustrate the scope of the present invention.

In one aspect, the present invention provides a process for preparing an organoaryl compound of the formula Ar'—R, comprising contacting an arylnitrile compound of the formula Ar'—CN with a compound of the formula (R)$_x$-M, in the presence of a nickel or palladium catalyst having a phosphine or phosphite ligand under conditions sufficient for the R group to become attached to the carbon atom bearing the nitrile group of the arylnitrile compound, displacing the nitrile substituent. In the formula above, M represents a magnesium or zinc optionally having additional ligands, the symbol Ar' represents a substituted or unsubstituted aryl group, R represents a substituted or unsubstituted member selected from the group consisting of aryl, alkenyl and alkyl, and the subscript x is an integer of from 1 to 3.

Preferably, (R)$_x$-M is an organomagnesium reagent having a formula selected from R$_2$Mg and RMgY, wherein Y is selected from Cl, Br, I, OR', SR' and PR'R", wherein each R' and R" is independently selected from substituted or unsubstituted (C$_1$-C$_8$)alkyl, substituted or unsubstituted aryl and substituted or unsubstituted aryl(C$_1$-C$_4$)alkyl. More preferably, the organomagnesium reagent has the formula RMgY, wherein R is as provided above and Y is selected from Cl, Br, OtBu, OEt, OiPr, OBHT (from 2,6-di-tert-butyl-4-methylphenol), SPh and PPh$_2$.

The present methods can be used with a variety of arylnitriles of the formula Ar'—CN. Preferably, the aryl group (Ar') is selected from substituted or unsubstituted phenyl, substituted or unsubstituted naphthyl, substituted or unsubstituted pyridyl, substituted or unsubstituted pyridazinyl and substituted or unsubstituted furanyl. More preferably, Ar' is either a substituted or unsubstituted phenyl or a substituted or unsubstituted pyridyl.

In one group of embodiments, R is a substituted or unsubstituted aryl group such that the product is a biaryl compound of the formula AR'—Ar. Suitable aryl groups Ar and Ar' include carbocyclic aryl groups, having only carbon atoms in the aromatic ring system and heterocyclic aryl groups, having one or more heteroatoms in the aromatic ring system. Typical carbocyclic aryl groups have 6-14 carbon atoms in the aromatic ring system. Preferred carbocyclic groups are phenyl, naphthyl and substituted phenyl or naphthyl groups. Typical heterocyclic aryl groups have 5-13 atoms in the aromatic ring system which comprises carbon atoms and one or more heteroatoms. Preferred heteroatoms are oxygen, sulfur, and nitrogen. Preferred heterocyclic aryl groups have 5 or 6 atoms in an aromatic ring comprising one or more heteroatoms selected from the group oxygen, sulfur and nitrogen, benz-fused derivatives thereof, and substituted derivatives thereof. Examples of preferred heterocyclic aryl groups include pyridyl, furyl, thiophenyl, pyrrolyl, their benz-fused derivatives quinolinyl, isoquinolinyl, benzfuryl, benzthiophenyl, indolyl, isoindolyl, and substituted derivatives thereof.

Generally, substituents in substituted aryl groups Ar and Ar' can be any substituent that does not interfere with the coupling reaction, including alkyl (preferably $C_1$-$C_{12}$), alkenyl (preferably $C_2$-$C_{12}$), alkynyl (preferably $C_2$-$C_{12}$), alkoxy (preferably $C_1$-$C_{12}$), acyloxy (preferably $C_1$-$C_{12}$), aryloxy, aryl, heteroaryl, F, Cl, OH, $NO_2$, COOH, CHO, $SO_3H$, $SO_2$, SOR, $NH_2$, NH-alkyl (preferably $C_1$-$C_{12}$), N-dialkyl (preferably $C_1$-$C_{12}$), haloalkyl (e.g., trihalomethyl), NHCO-alkyl (preferably $C_1$-$C_8$), CONH-alkyl (preferably $C_1$-$C_4$), CON-dialkyl (preferably $C_1$-$C_4$), COO-alkyl (preferably $C_1$-$C_{12}$), $CONH_2$, CO-alkyl (preferably $C_1$-$C_{12}$), NHCOH, NHCOO-alkyl (preferably $C_1$-$C_8$), CO-aryl, COO-aryl, $CHCHCO_2$-alkyl (preferably $C_1$-$C_{12}$), $CHCHCO_2H$, PO-diaryl, and PO-dialkyl (preferably $C_1$-$C_8$). One of skill in the art will understand that the presence of a substituent having an active hydrogen atom (e.g., OH, COOH, CONH-alkyl and the like) will consume an equivalent molar amount of the organomagnesium or organozinc reagent, such that an excess of the organometallic reagent will be desired for higher yield coupling reactions.

In this group of embodiments, the biaryl compounds of the general formula AR'—Ar are prepared by reacting an arylmagnesium or arylzinc reagent comprising the aryl group Ar bonded to magnesium or zinc with an arylnitrile of the formula Ar'—CN in the presence of a catalyst selected from the group consisting of nickel catalysts and palladium catalysts, each of which has a phosphorus ligand, preferably a phosphine or phosphite ligand.

Suitable arylmagnesium reagents are selected from the group consisting of arylmagnesium salts, diarylmagnesium compounds, or mixtures thereof. Arylmagnesium salts have the general formula ArMgY, wherein Ar is a substituted or unsubstituted aryl group and Y is an inorganic or organic salt anion. The identity of the anion Y can be varied but must not interfere with the reaction, which can be determined by routine experimentation. In one group of preferred embodiments, the arylmagnesium salts are arylmagnesium halides, also known as aryl Grignard reagents, of the general formula ArMgX, wherein X is a halide anion. Especially preferred are arylmagnesium chloride and arylmagnesium bromide reagents. Diaryl magnesium compounds having the general formula $Ar_2Mg$ are also useful. Arylmagnesium halides and diarylmagnesium compounds can be prepared from arylhalides and magnesium by methods known in the art. In another group of preferred embodiments, the arylmagnesium salt is an arylmagnesium alkoxide or aryloxide (e.g., ArMg(OR')) in which R' is selected from substituted or unsubstituted ($C_1$-$C_8$)alkyl, substituted or unsubstituted aryl and substituted or unsubstituted aryl($C_1$-$C_4$)alkyl. Particularly preferred groups for OR' include t-butoxide (O-tBu), ethoxide (OEt), isopropoxide (OiPr) and 2,6-di-t-butyl-4-methylphenoxide (OBHT). The alkoxide or aryloxide magnesium salts are generally prepared from the corresponding Grignard (MgBr or MgCl) reagents by reaction with an appropriate metal alkoxide reagent (e.g., lithium alkoxide, or the corresponding sodium or potassium salt) in an aprotic solvent. For example, phenylmagnesium bromide can be treated with lithium t-butoxide in ether to provide phenylmagnesium t-butoxide. Other suitable solvents for the preparation of arylmagnesium alkoxide or arylmagnesium aryloxide salts include THF, glyme, diglyme, dioxane, mixtures thereof, or mixtures with, for example, toluene.

Similarly, suitable arylzinc reagents are arylzinc species comprising the aryl group sigma bonded to zinc. Typical arylzinc reagents include those selected from the group consisting of arylzinc salts, arylzinc compounds, or mixtures thereof. Arylzinc salts are known in the art and have the general formula ArZnY, wherein Y is an inorganic or organic salt anion. As above, the identity of the anion Y can be varied but it must not interfere with the reaction, which can be determined by routine experimentation. Preferred arylzinc salts are arylzinc halides of the general formula ArZnX, wherein X is a halide anion. Especially preferred are arylzinc chloride and arylzinc bromide reagents. Arylzinc compounds are known in the art and include monoarylzinc compounds and diarylzinc compounds. Examples of monoarylzinc compounds include compounds of the general formula ArZnR, wherein R is an organo group which does not interfere with the reaction. Preferred arylzinc compounds are diaryl zinc compounds having the general formula $Ar_2Zn$. Triarylzincate anions having the general formula $Ar_3Zn^-$ are also suitable arylzinc reagents.

The arylzinc reagents may be obtained by various methods known in the art. For example, the corresponding arylhalide ArX, wherein X=Cl, Br, I, may be reacted with activated zinc to afford the corresponding arylzinc halide. A zinc salt may be reacted with a corresponding aryllithium reagent or arylmagnesium reagent to form the arylzinc reagent. Preferably, the zinc salt is reacted with one to two equivalents of aryllithium or arylmagnesium reagent to form the arylzinc salt, the diarylzinc compound, or mixtures thereof An aryllithium reagent or an arylmagnesium salt comprises one aryl equivalent; a zinc salt is reacted with one of them in a mole ratio of 1:1 to 1:3. A diarylmagnesium reagent comprises two aryl equivalents; a zinc salt is reacted with it in a mole ratio of 0.5:1 to 1:1. Suitable zinc salts for these preparations include salts having the general formula $ZnY_2$, wherein Y is defined as above. Preferred zinc salts are the zinc halides $ZnX_2$, wherein X is a halide ion. Especially preferred are zinc chloride and zinc bromide. Suitable arylmagnesium reagents for the preparation of arylzinc reagents are essentially those that have been described above for direct use in the methods of the present invention.

A variety of nickel and palladium catalysts can be used in the present methods, including those provided by nickel and palladium compounds and salts, in particular nickel(0) and palladium(0) compounds and nickel(II) and palladium(II) compounds and salts. In each instance, the catalyst will have at least one phosphorus ligand, preferably a phosphine or phosphite ligand. Suitable ligands include monodentate, bidentate, and tridentate ligands. In the case wherein the ligand is a bidentate or tridentate ligand, at least one of the ligating atoms is phosphorus. The remaining ligating atom will preferably be phosphorus or nitrogen. For monodentate ligands, the phosphorus ligand will generally have the formula:

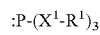

:P-$(X^1$-$R^1)_3$ wherein each $X^1$ independently represents a bond, O, S or $NR^2$, and each R' and $R^2$ independently represents an aryl, ($C_2$-$C_8$)alkenyl or (Cl-$C_8$)alkyl group, or when R' and $R^2$ are attached to a common nitrogen atom are combined to form a five- or six-membered ring (e.g., a pyrrolidinyl or piperidinyl ring).

Preferred ligands are triorganophosphine and triorganophosphite. Examples of preferred ligands include trialkylphosphines (e.g., trimethylphosphine, triethylphosphine, dimethylethylphosphine, and the like), triarylphosphines (e.g. triphenylphosphine), bidentate bis(diarylphosphino) compounds (e.g. 1,1'-bis(diphenylphosphino)ferrocene) and trialkyl- or triarylphosphites (e.g. triisopropylphosphite, trineopentylphosphite and triphenylphosphite). Still further preferred are those catalysts having a phosphine ligands selected from $Me_3P$, $Me_2PPh$, $Et_3P$, $MePPh_2$, $Me_2PCH_2CH_2PMe_2$, $Ph_3P$ and $(C_6H_{11})_3P$. Most preferred are those ligands illustrated in the working Examples herein. In one particularly preferred embodiment, the catalyst is $C_{12}Ni(PMe_3)_2$.

Suitable and optimal ratios of the ligand to catalyst metal depend on a number of other parameters, including the catalyst metal, whether nickel or palladium, the identity of the ligand, the concentration of the catalyst, the reaction temperature, the reactivity of the reactants, the solvent, and the like, and can be readily determined by routine experimentation. Typically the ratio of the ligand to the catalyst metal is in the range of 1:1 to 4:1. However, the amount of ligand in the reaction mixture may be in excess of the maximum ratio that could be bound to the catalyst metal.

The active catalyst may be prepared in advance of its introduction to the reaction mixture, or may be generated in the reaction mixture. The active catalyst may be provided by a preformed ligated nickel(0) or palladium(0) compound (e.g. tetrakis(triphenylphosphine)palladium(0), bis(triphenylphosphine)nickel(0) dicarbonyl) or may be provided by combining in solution, either ex situ or in situ to the reaction mixture, a suitable ligand with a suitable nickel(0) or palladium(0) source (e.g. bis(1,5-cyclooctadiene)-nickel(0), tris(dibenzylideneacetone)palladium(0)). When the catalyst is provided by a nickel(II) or palladium(II) compound or salt, the active catalyst is provided by its reduction either ex situ or in situ to the reaction mixture. Generally, either the arylzinc reagent or the arylmagnesium reagent in the reaction mixture is capable of reducing the nickel(II) or palladium(II) to generate the active catalyst in situ, with concomitant generation of the symmetrical biaryl Ar—Ar. This can be determined by routine experimentation. Suitable reductants for ex situ generation of the active catalyst from nickel(II) and palladium(II) sources are known in the art and include organomagnesium halide reagents (e.g. methylmagnesium halide) and various hydride reagents (e.g. sodium bis(2-methoxyethoxy)aluminum dihydride). Preferably the nickel(II) or palladium(II) is combined with ligand prior to its reduction. The nickel(II) or palladium(II) may be provided as a preformed ligated nickel (II) or palladium(II) compound (e.g. dichlorobis(triphenylphosphine)nickel(II), dichloro[1.1'-bis(triphenylphosphino)ferrocene]palladium(II)) or may be provided by combining in solution a suitable ligand with a suitable nickel (II) or palladium(II) compound (e.g. dichlorobis(acetonitrile)palladium(II)) or salt. Suitable nickel(II) and palladium(II) salts include the salts having the general formula $NiY'_2$ and $PdY'_2$, wherein Y' is a halogen, acetylacetonate or a carboxylate such as an acetate. Preferred nickel(II) or palladium(II) salts include the chlorides, bromides, carboxylates (e.g. formate, acetate, stearate) and acetylacetonates. Generally, anhydrous nickel and palladium salts are preferred.

The reaction of either an arylmagnesium or arylzinc reagent with the arylnitrile is typically conducted with a solvent that is reaction-inert. A reaction-inert solvent is a solvent system which does not react with the reactants or products of the reaction, or react unfavorably with the catalyst. The term "solvent system" is used to indicate that a single solvent or a mixture of two or more solvents can be used. Representative solvents are aromatic hydrocarbons such as benzene, toluene, xylene; aliphatic hydrocarbons such as pentane, hexane, heptane; acetonitrile; dialkyl ethers; and cyclic ethers, and mixtures thereof. The solvent system used need not bring about complete solution of the reactants.

Preferred solvents in the solvent system are ether solvents, including diethyl ether, diisopropyl ether, dibutylether, methyl-t-butylether, dimethoxyethane, diglyme, dibutyldiglyme, tetrahydrofuran, dioxane, and the like. It is generally preferred that the solvent system is anhydrous. In certain embodiments, however, it has been surprisingly found that a small amount of water can be beneficial to the catalyst activity. Whether small amounts of water are advantageous or detrimental in a specific embodiment can be determined by routine experimentation.

The ratio of the arylmagnesium or arylzinc reagent to the arylnitrile can be varied. Either reactant may be the limiting reactant and this choice can respond to other considerations, such as which is the more costly reactant to provide and which homocoupled by-product is more readily separated or removed to an acceptable level from the desired cross-coupled product. Generally the ratio of equivalents of arylmagnesium or arylzinc reagent to mole of arylnitrile ranges from 0.5:1 to 10:1, more preferably 1:1 to 3:1, and most preferably about 2:1. One mole of either a diarylmagnesium reagent or a diarylzinc reagent is counted as two equivalents of arylmagnesium reagent or arylzinc reagent, respectively. In typical embodiments, this ratio is in the range 1:1 to 1.5:1.

The mole ratio of the catalyst to the arylnitrile to be reacted is similarly variable, but should be a catalytic ratio less than about 1:10. The minimum amount of catalyst relative to the arylnitrile depends on the activity of the specific catalyst composition, the specific arylnitrile and arylmagnesium or arylzinc reagent to be reacted, the reaction temperature, the concentration of the reactants and catalyst in the solution, and the maximum time allowed for completion of the reaction, and can be readily determined by routine experimentation. In typical embodiments, a suitable mole ratio of the catalyst metal, nickel or palladium, to arylnitrile is in the range of 1:1000 to 1:10.

In typical embodiments, the reaction is suitably conducted at a temperature of from about 20° C. to 100° C., although higher temperature can be used in some embodiments.

The reaction components can be combined in essentially any order. For those reactions run at elevated temperatures, the reaction components can be combined prior to any heating to the reaction temperature, or one or more components may be added when the other components have been brought to the desired reaction temperature. The preferred order of addition for any specific embodiment can be determined by routine experimentation with a view towards both reaction performance and chemical engineering considerations.

The desired biaryl compound can be recovered and purified, if necessary, by known methods.

While the invention has been described in detail for preparing biaryl compounds, in another group of embodiments, R is a substituted or unsubstituted alkyl or alkenyl group, prefereably an alkyl or alkenyl group having from one to twelve carbon atoms. Accordingly, the product of this method is a compound of the formula Ar'—R wherein R is a substituted or unsubstituted alkyl or alkenyl group. In general, alkyl- or alkenylmagnesium reagents and alkyl- or alkenylzinc reagents can be substituted for the arylmagnesium reagents and arylzinc reagents described above. Moreover, a variety of alkyl- or alkenylmagnesium reagents and alkyl- or alkenylzinc reagents are available or can be prepared by well-known methods. For a review of organozinc reagents, see "Preparation and Applications of Functionalized Organozinc Compounds" P. Knochel, N. Millot, A. L. Rodriguez, C. E. Tucker, ORGANIC REACTIONS, Vol. 58, p. 417-731, 2001.

The present invention further provides compounds prepared by the methods described above and illustrated in the Examples herein.

Reaction Mixtures

In another aspect, the present invention provides reaction mixtures comprising an arylnitrile of the formula Ar'—CN, a nickel or palladium catalyst having a phosphine or phosphite ligand, and an organometallic reagent having the formula $(R)_x$-M; wherein the symbol Ar' represents a substituted or unsubstituted aryl group, R represents a substituted or unsubstituted member selected from the group consisting of aryl, arylalkyl, alkenyl and alkyl, the subscript x is an integer of from 1 to 3, and M is magnesium or zinc optionally having additional ligands, with the proviso that said Ar group does not contain a halogen substituent. In related embodiments, halogen substituents can be present if coupling of the R group at the carbon center bearing the halogen is also desired. In this instance, appropriate increases in the amount of organometallic reagent should be made to permit optimun reaction at each of the carbon-nitrile and carbon-halogen centers.

In general, the preferred components of the reaction mixtures are those components described above as preferred with reference to the methods and processes described herein.

Accordingly, in one group of embodiments, the reaction mixture contains an organometallic reagent that is an organomagnesium reagent having the formula RMgY, wherein Y is selected from Cl, Br, I, OR', SR' and PR'R", wherein each R' and R" is independently selected from substituted or unsubstituted $(C_1$-$C_8)$alkyl, substituted or unsubstituted aryl and substituted or unsubstituted aryl$(C_1$-$C_4)$alkyl. More preferably, the organomagnesium reagent has the formula RMgY, wherein R is as provided above and Y is selected from Cl, Br, OtBu, OEt, OiPr, OBHT, SPh and $PPh_2$. Particularly preferred embodiments are those in which R is substituted or unsubstituted aryl.

In still other preferred embodiments, the reaction mixture contains an organomagnesium reagent of the formula $R_2Mg$, wherein each R represents a substituted or unsubstituted member selected from the group consisting of aryl, arylalkyl, alkenyl and alkyl, more preferably aryl. Still further preferred are those embodiments in which each of the aryl groups are the same and are selected from substituted and unsubstituted phenyl, substituted and unsubstituted naphthyl, and substituted and unsubstituted pyridyl.

In related embodiments, the reaction mixture contains an organometallic reagent that is an organozinc reagent having the formula RZnY, wherein Y is selected from Cl, Br, I or OR' in which R' is a catacholate or pinacolate, or Y is an additional R group (e.g., $R_2Zn$). More preferably, the organozinc reagent has the formula RZnY, wherein R is as provided above and Y is selected from Cl or Br. Particularly preferred embodiments are those in which R is substituted or unsubstituted aryl.

Preferred arylnitriles in these reaction mixtures are those that have been described above. Particularly preferred arylnitriles are those of formula Ar'—CN wherein Ar' is selected from substituted and unsubstituted phenyl, substituted and unsubstituted pyridyl, and substituted and unsubstituted furanyl.

In certain preferred embodiments, the catalyst is a nickel catalyst selected from $Cl_2Ni(PMe_3)_2$, $Cl_2Ni(PEt_3)_2$, $Cl_2Ni(PPh_3)_2$, $Cl_2Ni(Me_2PPh)_2$, $Cl_2Ni(MePPh_2)_2$ and $Cl_2Ni(Me_2PCH_2CH_2PMe_2)$. In other preferred embodiments, the catalyst is prepared in situ from $Ni(acetylacetonate)_2$ and $PMe_3$.

In one group of particularly preferred embodiments, the reaction mixture comprises an organometallic reagent having the formula R-M-Y wherein R is substituted or unsubstituted aryl, M is Mg or Zn, Y is either Cl or Br, and the mixture further comprises a base selected from the group consisting of LiO—$(C_1$-$C_8)$alkyl, LiSPh and LiOBHT.

Still further preferred are those embodiments in which Ar'—CN is a substituted or unsubstituted benzonitrile, R is a substituted or unsubstituted aryl, Y is Cl or Br, and the mixture further comprises a base selected from LiO-$(C_1$-$C_8)$alkyl, LiSPh and LiOBHT.

Organomagnesium Reagents

In yet another aspect, the present invention provides an organomagnesium reagent having the formula $R^1MgY^1$, wherein $R^1$ is substituted or unsubstituted aryl or alkenyl and $Y^1$ is selected from S-aryl, S-$(C_1$-$C_8)$alkyl, P$((C_1$-$C_8)$alkyl$)_2$, P$(aryl)_2$ and P$((C_1$-$C_8)$alkyl$)$(aryl). Preferably, $Y^1$ is selected from SPh and $PPh_2$ wherein Ph is a substituted or unsubstititued phenyl.

In one group of embodiments, $R^1$ is substituted or unsubstituted aryl, more preferably, substituted or unsubstituted phenyl, substituted or unsubstituted naphthyl, substituted or unsubstituted pyridyl, substituted or unsubstituted pyridazinyl, and substituted or unsubstituted furanyl.

In another group of embodiments, R is a substituted or unsubstituted $(C_2$-$C_8)$alkenyl.

EXAMPLES

Example 1

This example illustrates the preparation of 4-phenylanisole by a nickel catalyzed coupling of 4-methoxybenzonitrile with phenylmagnesium chloride/lithium t-butoxide.

A solution of lithium t-butoxide in THF (4.4 mL of 1.0 M solution; 4.4 mmol) was treated at room temperature with phenylmagnesium chloride (2.8 mL; 4.0 mmol; 1.40 M in THF) and the resulting solution heated at 60° C. for 1 h. After cooling to room temperature, the reaction solution was treated with a solution of 4-methoxybenzonitrile (0.27 g, 2.0 mmol), dichlorobis(trimethylphosphine)nickel (0.028 g; 5 mol %), and tridecane (0.18 g; 1.0 mmol; internal GC standard) in THF (2 mL). The reaction mixture was then heated to 60° and stirred for 2 h. A sample was withdrawn and quenched in a mixture of 1 M sodium citrate (aq) and ether. GC analysis of the organic phase of the hydrolyzed reaction sample showed the presence of 1.82 mmol (91% yield) of 4-phenylanisole, 0.06 mmol of 4-methoxybenzophenone imine, 0.04 mmol of anisole, 0.17 mmol of biphenyl, 0.01 mmol of 4,4'-dimethoxybiphenyl, and no remaining 4-methoxybenzonitrile in the reaction mixture.

Example 2

In this example, a zinc reagent is used in place of the magnesium reagent of Example 1 to prepare 4-phenylanisole by the nickel catalyzed coupling of 4-methoxybenzonitrile with phenylzinc chloride.

A solution of zinc chloride (0.48 g; 3.5 mmol) in THF (5 mL) was treated at 0° C. with phenylmagnesium chloride (2.1 mL of a 1.40 M solution in THF; 3.0 mmol) and then stirred at room temperature for 30 min. The mixture of phenylzinc chloride thus obtained was then treated with a solution of 4-methoxybenzonitrile (0.27 g; 2.0 mmol), dichlorobis(trimethylphosphine)nickel (0.028 g; 5 mol %), and tridecane (0.18 g; 1.0 mmol; internal GC standard) in THF (2 mL) and heated at 60° C. for 8 h. A sample was withdrawn and quenched in a mixture of 1 M sodium citrate (aq) and ether. GC analysis of the organic phase of the hydrolyzed reaction sample showed the presence of 0.90 mmol (45% yield) of 4-phenylanisole, no 4-methoxybenzophenone imine, 0.38 mmol of anisole, 0.82 mmol of biphenyl, 0.23 mmol of 4,4'-dimethoxybiphenyl, and 0.09 mmol of 4-methoxybenzonitrile remaining in the reaction mixture.

Example 3

This example illustrates that use of an aryl Grignard compound (e.g., ArMgX; X=halide) instead of a derivatized aryl Grignard reagent (e.g., the adduct derived from ArMgX and LiOBu-t or LiSPh) in the Ni-catalyzed coupling reaction with benzonitriles. 4-phenylanisole is prepared by the nickel catalyzed coupling of 4-methoxybenzonitrile with phenylmagnesium chloride Phenylmagnesium chloride (2.1 mL of a 1.4 M solution in THF; 3.0 mmol) was diluted with additional THF (3 mL) and treated at room temperature with a solution of 4-methoxybenzonitrile (0.27 g; 2.0 mmol), dichlorobis(trimethylphosphine)nickel (0.028 g; 5 mol %), and tridecane (0.18 g; 1.0 mmol; internal GC standard) in THF (2 mL). The reaction was heated at 60° C. for 90 min and then a sample was withdrawn and quenched in a mixture of 1 M sodium citrate (aq) and ether. GC analysis of the organic phase of the hydrolyzed reaction sample showed the presence of 1.42 mmol (71% yield) of 4-phenylanisole, 0.36 mmol of 4-methoxybenzophenone imine, 0.01 mmol of anisole, 0.18 mmol of biphenyl, 0.02 mmol of 4,4'-dimethoxybiphenyl, and no remaining 4-methoxybenzonitrile in the reaction mixture.

Example 4

This example illustrates the preparation of 4-phenylanisole by the coupling of 4-methoxybenzonitrile with phenylmagnesium chloride/lithium t-butoxide using an in situ prepared nickel catalyst and further illustrates that the nickel catalyst may be provided by combining a nickel salt and the phosphine ligand, instead of utilizing a "preformed" complex.

The procedure was identical to Example 1, with the exception that the nickel catalyst used was derived in situ from a combination of anhydrous nickel acetylacetonate (0.026 g; 5 mol %) and trimethylphosphine (0.20 mL of 1 M solution in toluene; 10 mol %). GC analysis of the organic phase of the hydrolyzed reaction sample after 2 h at 60° C. showed the presence of 1.76 mmol (88% yield) of 4-phenylanisole, 0.11 mmol of 4-methoxybenzophenone imine, and no remaining 4-methoxybenzonitrile in the reaction mixture.

Example 5

This example illustrates the evaluation of various phosphine ligands for the nickel catalyst in this cross coupling reaction of aryl Grignard derivatives with benzonitriles. In addition to trimethylphosphine, other alkyl-substituted phosphines also afford viable nickel catalysts, but their efficency seems to be inversely proportional to their steric requirements (i.e., $Me_3P>Et_3P>$tricyclohexylphosphine). On the other hand, arylphosphine derivatives (e.g., $Ph_3P$ and $MePPh_2$) provide generally less effective nickel catalysts for this transformation. Chelating bis(phosphines), such as DMPE, also afford effective nickel catalysts for this transformation. Each of the phosphine ligands was evaluated in the preparation of 4-phenylanisole by the nickel catalyzed coupling of 4-methoxybenzonitrile with phenylmagnesium chloride/lithium t-butoxide.

The procedure was identical to Example 1, with the exception that the nickel catalyst used was derived in situ from a combination of anhydrous nickel acetylacetonate (0.026 g; 5 mol %) and the various phosphines listed below in the table [$Ph_3P$: 0.052 g; $Ph_2PMe$: 37 µL; $PhPMe_2$: 28 µL; $Et_3P$: 0.20 mL of 1M solution in THF; 1,2-bis(dimethylphosphino)ethane, "DMPE": 17 uL; $(C_6H_{11})_3P$: 0.056 g; 10 mol % of each phosphine used, except for DMPE (5 mol % used)]. GC analysis of the organic phase of the hydrolyzed reaction sample after 24 h at 60° C. provided the results shown below in the table.

TABLE

| Phosphine | Reaction Time | Ph—⬡—OMe Yield (mmol) | MeO—⬡—C(=NH)Ph (mmol) | NC—⬡—OMe (mmol) |
|---|---|---|---|---|
| $Ph_3P$ | 24 h | 0.44 | 0.98 | 0.07 |
|  | 2 h | 0.11 | 0.58 | 0.89 |
| $Ph_2PMe$ | 24 h | 1.06 | 0.65 | 0.03 |
|  | 2 h | 0.37 | 0.44 | 0.82 |
| $PhPMe_2$ | 24 h | 1.55 | 0.36 | 0 |
|  | 2 h | 0.90 | 0.29 | 0.52 |
| $Me_3P$* | 2 h | 1.76 | 0.11 | 0 |
| $Et_3P$ | 24 h | 1.49 | 0.36 | 0.02 |
|  | 2 h | 0.77 | 0.28 | 0.65 |
| $Me_2P(CH_2)_2PMe_2$ "DMPE" | 24 h | 1.02 | 0.50 | 0.25 |
|  | 2 h | 0.56 | 0.28 | 0.87 |
| $(C_6H_{11})_3P$ | 24 h | 0.15 | 1.14 | 0.24 |
|  | 2 h | 0.10 | 0.62 | 0.90 |

*This result is from Example 4, and is included here for direct comparison with the other phosphines.

Example 6

This example illustrates the preparation of 4-phenylanisole by the nickel catalyzed coupling of 4-methoxybenzonitrile with phenylmagnesium chloride/lithium ethoxide and further demonstrates that better results can be obtained in this coupling reaction when the lithium alkoxide used to derivatize the aryl Grignard reagent is relatively sterically bulky (i.e., better results obtained from use of LiOBu-t compared with LiOEt).

The procedure was identical to Example 1, with the exception that lithium ethoxide (4.4 mL of 1.0 M solution in THF; 4.4 mmol) was used instead of lithium t-butoxide. GC analysis of the organic phase of the hydrolyzed reaction sample after 2h at 60° C. showed the presence of 1.33 mmol (66% yield) of 4-phenylanisole, 0.16 mmol of 4-methoxybenzophenone imine, and 0.28 mmol of 4-methoxybenzonitrile remaining in the reaction mixture.

Example 7

This example illustrates the preparation of 4-phenylanisole by the nickel catalyzed coupling of 4-methoxybenzonitrile with phenylmagnesium chloride/lithium thiophenoxide and further shows that thiophenoxide anions, such as lithium thiophenoxide, serve as efficient derivatizers of the aryl Grignard reagents in this reaction.

The procedure was identical to Example 1, with the exception that lithium thiophenoxide (4.4 mL of 1.0 M solution in THF; 4.4 mmol) was used instead of lithium t-butoxide. GC analysis of the organic phase of the hydrolyzed reaction sample after 2h at 60° C. showed the presence of 1.94 mmol (97% yield) of 4-phenylanisole, 0.02 mmol of 4-methoxybenzophenone imine, and no remaining 4-methoxybenzonitrile in the reaction mixture.

Example 8

This example illustrates the preparation of 4-phenylanisole by the nickel catalyzed coupling of 4-methoxybenzonitrile with phenylmagnesium chloride/sodium t-butoxide and further demonstrates that sodium t-butoxide can function in a manner similar to lithium t-butoxide in the ability to derivatize the aryl Grignard reagent for the desired benzonitrile coupling reaction.

The procedure was identical to Example 1, with the exception that a solution of sodium t-butoxide (0.42 g; 4.4 mmol) in THF (4 mL) was used in place of the solution of lithium t-butoxide in THF. GC analysis of the organic phase of the hydrolyzed reaction sample after 2h at 60° C. showed the presence of 1.47 mmol (74% yield) of 4-phenylanisole, with only a trace of 4-methoxybenzonitrile (<2%) remaining in the reaction mixture.

Example 9

This example illustrates the preparation of 4-phenylanisole by the nickel catalyzed coupling of 4-methoxybenzonitrile with phenylmagnesium chloride/potassium t-butoxide and also demonstrates that sodium t-butoxide can function in a manner similar to lithium t-butoxide in the ability to derivatize the aryl Grignard reagent for the desired benzonitrile coupling reaction.

The procedure was identical to Example 1, with the exception that a solution of potassium t-butoxide (4.4 mL of 1.0 M solution in THF; 4.4 mmol) was used in place of the solution of lithium t-butoxide in THF. GC analysis of the organic phase of the hydrolyzed reaction sample after 4 h at 60° C. showed the presence of 1.54 mmol (77% yield) of 4-phenylanisole, and no remaining 4-methoxybenzonitrile.

Example 10

This example illustrates the preparation of 4-phenylanisole by the nickel catalyzed coupling of 4-methoxybenzonitrile using "phenyl Grignard reagent" prepared from an in situ reaction of phenyllithium with magnesium bromide.

A slurry of magnesium bromide (0.74 g; 4.0 mmol) in THF (3 mL) was treated at room temperature with phenyllithium (2.4 mL of 1.7 M solution; 4.0 mmol). The solution was heated at 60° C. for 30 min, and was then treated at 60° with lithium t-butoxide (4.4 mL of 1.0 M solution in THF; 4.4 mmol) and heating was continued for 1 h. The reaction solution was cooled to room temperature and treated with a solution of 4-methoxybenzonitrile (0.27 g, 2.0 mmol), dichlorobis(trimethylphosphine)nickel (0.028 g; 5 mol %), and tridecane (0.18 g; 1.0 mmol; internal GC standard) in THF (2 mL). The reaction was then heated to 60° and stirred for 2 h. A sample was withdrawn and quenched in a mixture of 1 M sodium citrate (aq) and ether. GC analysis of the organic phase of the hydrolyzed reaction sample showed the presence of 1.67 mmol (84% yield) of 4-phenylanisole, 0.18 mmol of 4-methoxybenzophenone imine, and no remaining 4-methoxybenzonitrile in the reaction mixture.

Example 11

This example illustrates the preparation of 4-phenylanisole by the palladium catalyzed coupling of 4-methoxybenzonitrile with phenylmagnesium chloride/lithium t-butoxide, and further demonstrates that a palladium catalyst may be used to effect the desired cross coupling reaction between a benzonitrile and organomagnesium derivative.

The procedure was identical to Example 1, with the exception that a palladium-based catalyst was used instead of a nickel catalyst, being derived in situ from a combination of palladium acetate (0.023 g; 5 mol %) and 2-dicyclohexylphosphino-2'-(N,N-dimethylamino)biphenyl (0.039 g; 5 mol %). GC analysis of the organic phase of the hydrolyzed reaction sample after 18 h at 60° C. showed the presence of 0.086 mmol (4.3% yield) of 4-phenylanisole and 1.27 mmol of remaining 4-methoxybenzonitrile in the reaction mixture.

Example 12

This example illustrates the preparation of 4-phenyltoluene by the nickel catalyzed coupling of 4-tolunitrile with phenylmagnesium chloride/lithium t-butoxide.

The procedure was identical to Example 1, with the exception that 4-tolunitrile (0.23 g; 2.0 mmol) was used as substrate instead of 4-methoxybenzonitrile. GC analysis of the organic phase of the hydrolyzed reaction sample after 2 h at 60° C. showed the presence of 1.85 mmol (92% yield) of 4-phenyltoluene, and no remaining 4-tolunitrile in the reaction mixture.

Example 13

This example illustrates the preparation of 3-(4'-methylphenyl)anisole by the nickel catalyzed coupling of 4-tolunitrile with 3-methoxyphenylmagnesium bromide/lithium t-butoxide, and further illustrates that the aryl Grignard reagent may contain functionality (e.g., ether groups) and still effectively participate in the desired cross coupling reaction.

The procedure was identical to Example 1, with the exception that 4-tolunitrile (0.23 g; 2.0 mmol) was used as substrate and 3-methoxyphenylmagnesium bromide (4.0 mL of 1.0 M solution in THF; 4.0 mmol) was used in place of phenylmagnesium chloride. GC analysis of the organic phase of the hydrolyzed reaction sample after 2 h at 60° C. showed the presence of 1.83 mmol (92% yield) of 3-(4'-methylphenyl)anisole and no remaining 4-tolunitrile in the reaction mixture.

Example 14

This example illustrates the preparation of 4,4-dimethyl-2-(4'-methyl-biphenyl-4-yl)-2-oxazoline by the nickel catalyzed coupling of 4-tolunitrile with the Grignard reagent of 4,4-dimethyl-2-(4-bromophenyl)-2-oxazoline/lithium t-butoxide and further illustrates that the aryl Grignard reagent may contain heterocyclic functionality and still effectively participate in the desired cross coupling reaction.

To a mixture of magnesium turnings (0.15 g; 6.0 mmol) in THF (3 mL) was added 4,4-dimethyl-2-(4-bromophenyl)-2-oxazoline (0.77 g; 3.0 mmol), and the reaction stirred at room temperature for 1 h to complete the formation of the Grignard reagent. The solution of Grignard reagent was then treated with lithium t-butoxide (4.4 mL of 1.0 M solution in THF; 4.4 mmol) and heated at 60° C. for 1 h. After cooling to room temperature, the reaction solution was treated with a solution of 4-tolunitrile (0.23 g, 2.0 mmol), dichlorobis(trimethylphosphine)nickel (0.028 g; 5 mol %), and tridecane (0.18 g; 1.0 mmol; internal GC standard) in THF (2 mL). The reaction mixture was heated to 60° and stirred for 6 h. A sample was withdrawn and quenched in a mixture of 1 M sodium citrate (aq) and ether. GC analysis of the organic phase of the hydrolyzed reaction sample showed the presence of 1.76 mmol (88% yield) of 4,4-dimethyl-2-(4'-methyl-biphenyl-4-yl)-2-oxazoline and 0.13 mmol of remaining 4-tolunitrile in the reaction mixture.

Example 15

This example illustrates the preparation of 4-phenyltoluene by the nickel catalyzed coupling of benzonitrile with 4-methylphenylmagnesium bromide/lithium t-butoxide and further illustrates that the benzonitrile substrate need not contain any potentially "activating" substituents to allow efficient participation in the desired cross coupling reaction.

The procedure was identical to Example 1, with the exception that benzonitrile (0.21 g; 2.0 mmol) was used as substrate and 4-methylphenylmagnesium bromide (4.3 mL of 0.93 M solution in THF; 4.0 mmol) was used in place of phenylmagnesium chloride. GC analysis of the organic phase of the hydrolyzed reaction sample after 2 h at 60° C. showed the presence of 1.76 mmol (88% yield) of 4-phenyltoluene and only a trace (<2%) of benzonitrile remaining in the reaction mixture.

Example 16

This example illustrates the preparation of 4-(4'-fluorophenyl)toluene by the nickel catalyzed coupling of 4-fluorobenzonitrile with phenylmagnesium chloride/lithium t-butoxide and further illustrates that the benzonitrile substrate may contain a fluoro substituent and still efficiently participate in the desired cross coupling reaction.

The procedure was identical to Example 1, with the exception that 4-fluorobenzonitrile (0.24 g; 2.0 mmol) was used as substrate and 4-methylphenylmagnesium bromide (4.3 mL of 0.93 M solution in THF; 4.0 mmol) was used in place of phenylmagnesium chloride. GC analysis of the organic phase of the hydrolyzed reaction sample after 2 h at 60° C. showed the presence of 1.65 mmol (82% yield) of 4-(4'-fluorophenyl)toluene and no 4-fluorobenzonitrile remaining in the reaction mixture.

Example 17

This example illustrates the preparation of 4-(dimethylamino)biphenyl by the nickel catalyzed coupling of 4-(dimethylamino)benzonitrile with phenylmagnesium chloride/lithium t-butoxide and further illustrates that the benzonitrile substrate may contain an amino substituent and still efficiently participate in the desired cross coupling reaction.

The procedure was identical to Example 1, with the exception that 4-(dimethylamino)benzonitrile (0.23 g; 2.0 mmol) was used as substrate instead of 4-methoxybenzonitrile. GC analysis of the organic phase of the hydrolyzed reaction sample after 6 h at 60° C. showed the presence of 1.64 mmol (82% yield) of 4-(dimethylamino)biphenyl, and no remaining 4-(dimethylamino)benzonitrile in the reaction mixture.

Example 18

This example illustrate the preparation of t-butyl 3-phenylbenzoate by the nickel catalyzed coupling of t-butyl 3-cyanobenzoate with phenylmagnesium chloride/lithium thiophenoxide and further illustrates that the benzonitrile substrate may contain an ester substituent and still efficiently participate in the desired cross coupling reaction. In addition, this example shows that lithium thiophenoxide can serve as an efficient derivatizer of the aryl Grignard reagent in this reaction.

The procedure was identical to Example 1, with the exception that t-butyl 3-cyanobenzoate (0.41 g; 2.0 mmol) was used as substrate instead of 4-methoxybenzonitrile and that lithium thiophenoxide (4.4 mL of 1.0 M solution in THF; 4.4 mmol) was used instead of lithium t-butoxide. GC analysis of the organic phase of the hydrolyzed reaction sample after 1 h at room temperature showed the presence of 1.87 mmol (93% yield) of t-butyl 3-phenylbenzoate and no remaining t-butyl 3-cyanobenzoate in the reaction mixture.

Example 19

This example illustates the preparation of 2-phenylpyridine by the nickel catalyzed coupling of 2-cyanopyridine with phenylmagnesium chloride/lithium t-butoxide and further illustrates that a cyanopyridine substrate can efficiently participate in the desired cross coupling reaction.

The procedure was identical to Example 1, with the exception that 2-cyanopyridine (0.21 g; 2.0 mmol) was used as substrate instead of 4-methoxybenzonitrile. GC analysis of the organic phase of the hydrolyzed reaction sample after 24 h at room temperature showed the presence of 1.70 mmol (85% yield) of 2-phenylpyridine, and no remaining 2-cyanopyridine in the reaction mixture.

Example 20

This example illustrates the preparation of 3-phenylpyridine by the nickel catalyzed coupling of 3-cyanopyridine with phenylmagnesium chloride/lithium t-butoxide and further illustrates that a cyanopyridine substrate can efficiently participate in the desired cross coupling reaction.

The procedure was identical to Example 1, with the exception that 3-cyanopyridine (0.21 g; 2.0 mmol) was used as substrate (instead of 4-methoxybenzonitrile) and it was added as a solution in THF (2 mL) over a 10-15 minute period to the reaction mixture containing PhMgCl/LiOBu-t and Ni catalyst. GC analysis of the organic phase of the hydrolyzed reaction sample after 1 h at 60° C. showed the presence of 1.39 mmol (69% yield) of 3-phenylpyridine, and no remaining 3-cyanopyridine in the reaction mixture.

Example 21

This example illustrates the preparation of 3-phenylpyridine by the nickel catalyzed coupling of 3-cyanopyridine with phenylmagnesium chloride/"LiOBHT" and further illustrates that a cyanopyridine substrate can efficiently participate in the desired cross coupling reaction. In addition, this example also illustrates that the aryl Grignard may be derivatized with the lithium salt of "OBHT" to provide an efficent cross coupling reagent for this synthetic transformation.

A solution of 2,6-di-t-butyl-4-methylphenol ("HOBHT"; 0.97 g; 4.4 mmol) in THF (4 mL) was treated at 0° C. with n-butyllithium (2.2 mL of 2.0 M solution in hexane; 4.4 mmol). The reaction was then warmed to room temperature to complete the preparation of the corresponding lithium phenoxide ("LiOBHT"). The reaction mixture was then treated with phenylmagnesium chloride (2.8 mL of 1.40 M solution in THF; 4.0 mmol) and the resultant mixture heated at 60° C. for 1 h. The reaction mixture was cooled to room temperature and to it added a solution of 3-cyanopyridine (0.21 g; 2.0 mmol), dichlorobis(trimethylphosphine)-nickel (0.028 g; 5 mol %), and tridecane (0.18 g; 1.0 mmol; internal GC standard) in THF (2 mL). The reaction mixture was then stirred at room temperature for 6 h. A sample was withdrawn and quenched in a mixture of 1 M sodium citrate (aq) and ether. GC analysis of the organic phase of the hydrolyzed reaction sample showed the presence of 1.61 mmol (80% yield) of 3-phenylpyridine, and 0.04 mmol of 3-cyanopyridine remaining in the reaction mixture.

Example 22

This example illustrates the preparation of 4-phenylpyridine by the nickel catalyzed coupling of 4-cyanopyridine with phenylmagnesium chloride/"LiOBHT" and further illustrates that a cyanopyridine substrate can efficiently participate in the desired cross coupling reaction. In addition, this example also illustrates that the aryl Grignard may be derivatized with the lithium salt of "HOBHT" to provide an efficent cross coupling reagent for this synthetic transformation.

The procedure was identical to Example 21, with the exception that 4-cyanopyridine (0.21 g; 2.0 mmol) was used as substrate instead of 3-cyanopyridine. GC analysis of the organic phase of the hydrolyzed reaction sample after 6 h at room temperature showed the presence of 1.49 mmol (75% yield) of 4-phenylpyridine, and no remaining 4-cyanopyridne in the-reaction mixture.

Example 23

This example illustrates the preparation of 4-phenylpyridine by the nickel catalyzed coupling of 4-cyanopyridine with phenylmagnesium chloride/lithium thiophenoxide and further illustrates that a cyanopyridine substrate can efficiently participate in the desired cross coupling reaction. In addition, this example shows that lithium thiophenoxide can serve as an efficient derivatizer of the aryl Grignard reagent in this reaction.

In a 1 L 3-neck flask, equipped with a mechanical stirrer, were mixed phenyl magnesium chloride (96.1 mL; 192 mmol; 2.00 M in THF) and lithium thiophenoxide (211 mL; 211 mmol; 1.00 M THF) under a blanket of nitrogen. This mixture was heated to 60° C. for 1 h, and then cooled to 0-5° C. with an ice bath. In a separate 150 mL flask, nickel acetylacetonate ("anhydrous"; 0.617 g; 2.40 mmol; 0.025 equiv.) was dissolved under nitrogen in anhydrous THF (100 mL). To this green solution was added trimethylphosphine (4.8 mL; 4.80 mmol; 1.00 M in toluene; 0.05 equiv.) forming a blue solution. After stirring for 10 min, solid 4-cyanopyridine (10.0 g; 96.1 mmol; 1 equiv.) was added to the catalyst mixture forming a green solution. This solution was added via addition funnel to the PhMgCl/PhSLi reaction solution at a rate which maintained the reaction temperature below 15° C. After the addition was complete, the reaction was heated at 60° C. for 2 h. The reaction was then allowed to cool to room temperature, and was poured into 1M aqueous sodium citrate (500 mL). The organic layer was separated and the aqueous layer extracted three times with MTBE (265 mL each). The combined organic phase was extracted three times with 2 N aqueous HCl (250 mL each) and this combined aqueous extract was basified to pH 12 with 1 N aqueous NaOH. This mixture was then extracted three times with MTBE (330 mL each) and the combined organic phase was dried over anhydrous magnesium sulfate. After filtration of the drying agent, solvent was removed in vacuo leaving 14.1 g (91% yield) of 4-phenylpyridine as a light yellow solid. GC analysis of the product showed it to be >95% pure.

Example 24

This example illustrates the preparation of 4-phenylpyridine by the nickel catalyzed coupling of 4-cyanopyridine with phenylmagnesium chloride/lithium diphenylphosphide and further illustrates that a cyanopyridine substrate can efficiently participate in the desired cross coupling reaction. In addition, this example shows that lithium diphenylphosphide can serve as an efficient derivatizer of the aryl Grignard reagent in this reaction.

The procedure was identical to Example 1, with the exception that 4-cyanopyridine (0.21 g; 2.0 mmol) was used as substrate instead of 4-methoxybenzonitrile and that lithium diphenylphosphide (8.8 mL of 0.50 M solution in THF; 4.4 mmol) was used instead of lithium t-butoxide. GC analysis of the organic phase of the hydrolyzed reaction sample after 2h at room temperature showed the presence of 1.36 mmol (68% yield) of 4-phenylpyridine and 0.22 mmol of 4-cyanopyridine remaining in the reaction mixture.

Example 25

This example illustrates the preparation of 2-phenylfuran by the nickel catalyzed coupling of 2-cyanofuran with phenylmagnesium chloride/lithium t-butoxide and further illustrates that the benzonitrile substrate may be a heterocyclic aromatic derivative, such as a cyanofuran, and still efficiently participate in the desired cross coupling reaction.

The procedure was identical to Example 1, with the exception that 2-cyanofuran (0.19 g; 2.0 mmol) was used as substrate and 4-methylphenylmagnesium bromide (4.3 mL of 0.93 M solution in THF; 4.0 mmol) was used in place of phenylmagnesium chloride. GC analysis of the organic phase of the hydrolyzed reaction sample after 2 h at 60° C. showed the presence of 1.57 mmol (78% yield) of 2-phenylfuran.

Example 26

This example illustrates the cross coupling of 4-chlorobenzonitrile with phenylzinc chloride catalyzed by $Cl_2Ni(PMe_3)_2$ and further illustrates that a nickel catalyst possessing a methylphosphine-containing ligand labilizes the benzonitrile C—CN bond in addition to the aryl C—Cl bond toward cross coupling with the arylzinc reagent.

The procedure was identical to Example 2, with the exception that 4-chlorobenzonitrile (0.28 g; 2.0 mmol) was used as substrate instead of 4-methoxybenzonitrile. GC analysis of the organic phase of the hydrolyzed reaction sample after 18 h at 60° C. showed only a small amount (0.04 mmol) of 4-chlorobenzonitrile remaining in the reaction mixture, along with the presence of significant amounts (0.1-0.2 mmol) of 4-chlorobiphenyl, 4-phenylbenzonitrile, and p-terphenyl. Also detected in the reaction mixture by GCMS analysis were lower levels of 4,4'-dichlorobiphenyl, 4-(4'-chlorophenyl)benzonitrile, 4-cyano-p-terphenyl, 4-chloro-p-terphenyl, p-tetraphenyl, 4-cyano-p-tetraphenyl, and 4-chloro-p-tetraphenyl.

Example 27

This example illustrates the cross coupling of 4-chlorobenzonitrile with phenylzinc chloride catalyzed by $Cl_2Ni(PPh_3)_2$ and further illustrates that a nickel catalyst possessing triphenylphosphine ligands, and not methylphosphine-containing ligands, labilizes only the aryl C—Cl bond (and not the benzonitrile C—CN bond) toward cross coupling with the arylzinc reagent.

The procedure was identical to Example 2, with the exception that 4-chlorobenzonitrile (0.28 g; 2.0 mmol) was used as substrate (instead of 4-methoxybenzonitrile) and dichlorobis(triphenylphosphine)nickel (0.065 g; 5 mol %) was used as catalyst. GC analysis of the hydrolyzed reaction sample after 2 h at room temperature showed the complete consumption of 4-chlorobenzonitrile and the presence of 1.83 mmol of 4-phenylbenzonitrile and only a trace amount (<0.03 mmol) of p-terphenyl. No 4-chlorobiphenyl was detected in the reaction mixture.

Example 28

This example illustrates the preparation of p-xylene by the nickel catalyzed coupling of 4-tolunitrile with methylmagnesium chloride/lithium t-butoxide and further illustrates that alkyl Grignard reagents, in addition to aryl Grignard reagents, also undergo cross coupling with benzonitriles to afford the corresponding alkylated aromatics.

A solution of lithium t-butoxide in THF (4.4 mL of 1.0 M solution; 4.4 mmol) was treated at room temperature with methylmagnesium chloride (1.4 mL; 4.0 mmol; 2.83 M in THF) and the resulting solution heated at 60° C. for 1 h. After cooling to room temperature, the reaction solution was treated with a solution of 4-tolunitrile (0.23 g, 2.0 mmol), dichlorobis(trimethylphosphine)nickel (0.028 g; 5 mol %), and tridecane (0.18 g; 1.0 mmol; internal GC standard) in THF (2 mL). The reaction mixture was heated to 60° and stirred for 4 h. A sample was withdrawn and quenched in a mixture of 1 M sodium citrate (aq) and ether. GC analysis of the organic phase of the hydrolyzed reaction sample showed the presence of 1.32 mmol (66% yield) of p-xylene, and no remaining 4-tolunitrile in the reaction mixture.

Example 29

This example illustrates the preparation of 4-n-butyltoluene by the nickel catalyzed coupling of 4-tolunitrile with n-butylmagnesium chloride/lithium t-butoxide and further illustrates that alkyl Grignard reagents, in addition to aryl Grignard reagents, also undergo cross coupling with benzonitriles to afford the corresponding alkylated aromatics.

A solution of lithium t-butoxide in THF (4.4 mL of 1.0 M solution; 4.4 mmol) was treated at room temperature with n-butylmagnesium chloride (2.9 mL; 4.0 mmol; 1.36 M in THF) and the resulting solution heated at 60° C. for 1 h. After cooling to room temperature, the reaction solution was treated with a solution of 4-tolunitrile (0.23 g, 2.0 mmol), dichlorobis(trimethylphosphine)nickel (0.028 g; 5 mol %), and tridecane (0.18 g; 1.0 mmol; internal GC standard) in THF (2 mL). The reaction mixture was heated to 60° and stirred for 4 h. A sample was withdrawn and quenched in a mixture of I M sodium citrate (aq) and ether. GC analysis of the organic phase of the hydrolyzed reaction sample showed the presence of 0.86 mmol (43% yield) of 4-n-butyltoluene, and no remaining 4-tolunitrile in the reaction mixture.

Example 30

This example illustrates the preparation of 4-(1-propenyl)anisole by the nickel catalyzed coupling of 4-methoxybenzonitrile with 1-propenylmagnesium bromide/lithium t-butoxide and further illustrates that alkenyl Grignard reagents, in addition to aryl Grignard reagents, also undergo cross coupling with benzonitriles to afford the corresponding alkenylated aromatics.

A solution of lithium t-butoxide in THF (4.4 mL of 1.0 M solution; 4.4 mmol) was treated at room temperature with 1-propenylmagnesium bromide (7.27 mL; 4.0 mmol; 0.55 M in THF; mixture of cis and trans isomers) and the resulting solution heated at 60° C. for 1 h. After cooling to room temperature, the reaction solution was treated with a solution of 4-methoxybenzonitrile (0.27 g, 2.0 mmol), dichlorobis(trimethylphosphine)nickel (0.028 g; 5 mol %), and tridecane (0.18 g; 1.0 mmol; internal GC standard) in THF (2 mL). The reaction mixture was heated to 60° and stirred for 2 h. A sample was withdrawn and quenched in a mixture of 1 M sodium citrate (aq) and ether. GC analysis of the organic phase of the hydrolyzed reaction sample showed the presence of 1.39 mmol (70% yield) of cis and trans 4-(1-propenyl)anisole, and 0.026 mmol of remaining 4-methoxybenzonitrile in the reaction mixture.

Example 31

This example illustrates the preparation of 2-(4'-methylphenyl)pyridine by the nickel catalyzed coupling of 4-tolunitrile with 2-pyridylmagnesium chloride/lithium thiophenoxide A solution of i-propylmagnesium chloride (2.0 mL; 4.2 mmol; 2.10 M in THF) was diluted with THF (3 mL) and to it added 2-bromopyridine (0.38 mL; 4.0 mmol). The reaction was stirred at room temperature for 2 h, and then was concentrated in vacuo. The 2-pyridylmagnesium chloride residue (free of isopropyl bromide) was treated at room temperature with lithium thiophenoxide (4.4 mL; 4.4 mmol; 1.0 M in THF) and then heated at 60° C. for 1 h. After cooling to room temperature, the reaction solution was treated with a solution of 4-tolunitrile (0.23 g, 2.0 mmol), dichlorobis(trimethylphosphine)nickel (0.028 g; 5 mol %), and tridecane (0.18 g; 1.0 mmol; internal GC standard) in THF (2 mL). The reaction mixture was then heated to 60° and stirred for 1 h. A sample was withdrawn and quenched in a mixture of 1 M sodium citrate (aq) and ether. GC analysis of the organic phase of the hydrolyzed reaction sample showed the presence of 0.77 mmol (38% yield) of 2-(4'-methylphenyl)pyridine, and 0.14 mmol of remaining 4-tolunitrile in the reaction mixture.

Example 32

This example illustrates the preparation of 4-(1-propenyl)anisole by the Ni catalyzed coupling ($Ni(acac)_2$, neopentylphosphite) of 4-methoxybenzonitrile and a modified 1-propenyl Grignard reagent.

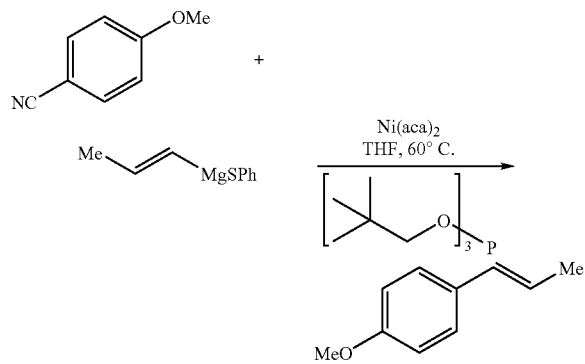

1-Propenyl magnesium bromide (8.0 mL in THF, 4.0 mmol) was added dropwise to PhSLi (4.5 mL in THF, 4.5 mmol) at rt. The reaction was warmed to 60° C. for 1.5 h. The organomagnesium reagent was then cooled to rt and charged into a THF (4 mL) solution containing 4-methoxybenzonitrile (272 mg, 2.0 mmol), Ni(acac)$_2$ (31 mg, 0.121 mmol), neopentylphosphite (66 mg, 0.226 mmol) and tridecane (188 mg, 1.0 mmol) as an internal standard. The resulting mixture was stirred at 60 ° C. for 14 h. An aliquot was taken from the reaction mixture and was treated with a 1 M sodium citrate solution. Extraction with ether provided a sample for GC analysis. This indicated the formation of an E/Z mixture of the desired styrene derivative (15% as a E/Z mixture) and 4-methoxybenzonitrile (17%).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A process for preparing an organoaryl compound of the formula Ar'—R comprising contacting an arylnitrile compound of the formula Ar'—CN with a compound of the formula (R)$_x$-M, in the presence of a nickel or palladium catalyst having a phosphine or phosphate ligand under conditions sufficient for said R group to become attached to the carbon atom bearing the nitrile group of said arylnitrile compound; wherein M is magnesium or zinc optionally having additional ligands, the symbol Ar' represents a substituted or unsubstituted aryl group, R represents a substituted or unsubstituted member selected from the group consisting of aryl, alkenyl and alkyl, and the subscript x is an integer of from 1 to 3.

2. A process in accordance with claim 1, wherein (R)$_x$-M is an organomagnesium compound having a formula selected from the group consisting of:

$R_2Mg$ and $RMgY$ wherein Y is selected from the group consisting of Cl, Br, I, OR', SR', and PR'R" wherein each R' and R" is independently selected from the group consisting of substituted or unsubstituted (C$_1$-C$_8$)alkyl, substituted or unsubstituted aryl and substituted or unsubstituted aryl(C$_1$-C$_4$)alkyl.

3. A process in accordance with claim 2, wherein said organomagnesium compound has the formula RMgY wherein Y is a member selected from the group consisting of Cl, Br, OtBu, OEt, OiPr, OBHT, SPh and PPh$_2$.

4. A process in accordance with claim 1, wherein Ar' is selected from the group consisting of substituted or unsubstituted phenyl, substituted or unsubstituted naphthyl, substituted or unsubstituted pyridyl, substituted or unsubstituted pyridazinyl, and substituted or unsubstituted furanyl.

5. A process in accordance with claim 4, wherein R is a substituted or unsubstituted aryl group.

6. A process in accordance with claim 5, wherein R is a substituted or unsubstituted phenyl group.

7. A process in accordance with claim 1, wherein said catalyst is a nickel catalyst.

8. A process in accordance with claim 1, wherein said phosphine ligand is selected from the group consisting of Me$_3$P, Me$_2$PPh, Et$_3$P, MePPh$_2$, Me$_2$PCH$_2$CH$_2$PMe$_2$, Ph$_3$P and (C$_6$H$_{11}$)$_3$P.

9. A process in accordance with claim 1, wherein said catalyst is Cl$_2$Ni(PMe$_3$)$_2$.

10. A process in accordance with claim 1, wherein said catalyst is prepared from Ni(acetylacetonate)$_2$ and PMe$_3$.

* * * * *